United States Patent [19]

Saias

[11] Patent Number: 4,518,606
[45] Date of Patent: May 21, 1985

[54] PHARMACEUTICAL COMPOSITIONS

[75] Inventor: Edmond Saias, Moulineaux, France

[73] Assignee: Beecham Group Limited, England

[21] Appl. No.: 396,711

[22] Filed: Jul. 9, 1982

Related U.S. Application Data

[63] Continuation of Ser. No. 204,847, Nov. 7, 1980, abandoned.

[30] Foreign Application Priority Data

Nov. 8, 1979 [GB] United Kingdom ............... 7938767

[51] Int. Cl.$^3$ ............................................. A61K 31/43
[52] U.S. Cl. .................................................... 514/197
[58] Field of Search .......................................... 424/271

[56] References Cited

U.S. PATENT DOCUMENTS

| | | | |
|---|---|---|---|
| 2,829,085 | 4/1958 | Gerber et al. | 424/271 |
| 2,966,442 | 12/1960 | Elias et al. | 424/271 |
| 3,070,507 | 12/1962 | Sponnoble | 424/271 |
| 4,029,804 | 6/1977 | Clark et al. | 424/271 |

Primary Examiner—Jerome D. Goldberg
Attorney, Agent, or Firm—Jacobs & Jacobs

[57] ABSTRACT

A pharmaceutical composition for injection which comprises an aqueous sterile solution of a penicillin or salt thereof and from 1 to 10% of benzyl alcohol, a two-pack container or two-part syringe wherein one pack or part contains a penicillin or salt thereof in the form of a dry powder and the second pack or part contains an aqueous solution of benzyl alcohol, such that mixing the contents of the two packs or parts produces an aqueous solution of the penicillin and from 1 to 10% of benzyl alcohol, and a two-pack container or two-part syringe wherein one pack or part contains a penicillin in a solid free acid form, and the second part contains an aqueous solution of benzyl alcohol and substantially one equivalent of a basic pharmaceutically acceptable salt, such that mixing the contents of the two packs or parts produces an aqueous solution of a salt of the penicillin and from 1 to 10% of benzyl alcohol.

3 Claims, No Drawings

PHARMACEUTICAL COMPOSITIONS

This application is a continuation of application Ser. No. 204,847 filed Nov. 7, 1980, and now abandoned.

This invention relates to pharmaceutical compositions suitable for injection. In particular it relates to compositions of certain penicillins, adapted for intramuscular injection.

It is desirable that any antibiotic should be made available in a form suitable for administration by injection, as well as for oral administration. Intramuscular injection is often a convenient route of administration. However some penicillins are not well absorbed by this route. It has now been found that injectable solutions of certain penicillins containing a small proportion of benzyl alcohol produce, after intramuscular administration, higher blood levels of the antibiotic, and the peak concentration is achieved more rapidly than with solutions without benzyl alcohol.

Accordingly the present invention provides a pharmaceutical composition adapted for intramuscular injection, which comprises an aqueous sterile solution of from 1 to 10% of benzyl alcohol, and a penicillin of formula (I) or a salt thereof:

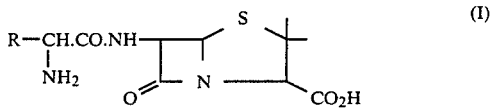

wherein R is an aryl group.

Suitable groups R include phenyl; mono-substituted phenyl where the substituent is halogen, hydroxy, $C_{1-6}$ alkoxy, nitro, amino, $C_{1-6}$ alkyl, $C_{1-6}$ haloalkyl, $C_{1-6}$ alkylcarbonyloxy, or $C_{1-6}$ alkyl sulphonylamino (for example —$NHSO_2CH_3$); or di-substituted phenyl where the substituents are selected from hydroxy, halogen, methoxy, acetoxy and amino.

For example, the group R may represent phenyl; mono-substituted phenyl where the substituent is fluorine, chlorine, hydroxy, methoxy, nitro, amino, acetoxy or trifluoromethyl; or di-substituted phenyl where the substituents are selected from acetoxy and methoxy.

Preferred values for R include phenyl and p-hydroxyphenyl.

All percentages herein are percentages by weight of the aqueous solution.

The penicillin salt may be prepared as a dry powder suitable for dissolution shortly before use, and this powder may conveniently be supplied in association with a container of an aqueous solution of benzyl alcohol for dissolution of the salt. In this way the proportion of benzyl alcohol to water in the solvent can more closely be controlled.

From a second aspect therefore, the invention provides a two-pack container or two-part syringe wherein one pack or part contains a penicillin of formula (I) herein or a salt thereof in the form of a dry powder and the second pack or part contains an aqueous solution of benzyl alcohol, such that mixing the contents of the two packs or parts produces an aqueous solution of the penicillin and from 1 to 10% of benzyl alcohol.

The benzyl alcohol employed in this invention should meet the specifications of Pharmacopoeias and in particular should be free from oxidising agents for example benzaldehyde and peroxides. The benzyl alcohol is suitably present in the injectable solutions in the range 2 to 10%, preferably 2 to 5%, especially from 3 to 4%. The water employed in the solution must be sterile and should be in accordance with the definitions of "water for injection" as described in U.S. Pharmacopoeia, 1973, page 500.

Suitable salts of penicillins for use in this invention include alkali metal salts, and in particular the sodium salt.

The penicillin salt will initially be formed as a dry powder. For example, for the sodium salt a suspension or solution of the penicillin in an appropriate solvent may be treated with sodium hydroxide, sodium carbonate or sodium bicarbonate to produce an aqueous solution of the sodium salt of the penicillin. The amount of alkali used will be about 1.0 equivalent. A slight excess is often required to obtain complete dissolution but this should be kept to a minimum as excess alkali causes rapid degradation of the penicillin and unacceptably high pH levels. This solution may then be conveniently reduced to a powder in conventional manner by precipitation, freeze-drying or spray-drying.

The penicillins of formula (I) and their salts may be employed in the compositions of this invention either alone or in a formulation with another penicillin, such as cloxacillin or flucloxacillin, or a β-lactamase inhibitor such as clavulanic acid.

Preferred penicillins of formula (I) include ampicillin and amoxycillin.

Suitable formulations include ampicillin/cloxacillin, ampicillin/flucloxacillin; amoxycillin/flucloxacillin and amoxycillin/clavulanic acid.

A preferred penicillin for use in the compositions of this invention is amoxycillin.

Amoxycillin is the generic name for the penicillin 6-[D(—)-α-amino-p-hydroxyphenylacetamido]-penicillanic acid which can also be called D-(—)-α-amino-p-hydroxy-benzylpenicillin. It has the structural formula (II):

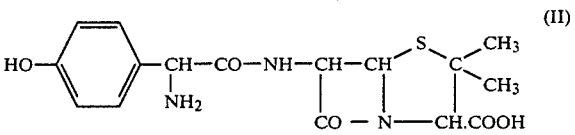

Amoxycillin is described in British Pat. No. 1,241,844.

One particularly advantageous method for the preparation of solid sodium amoxycillin for the composition of this invention comprises spray-drying a solution of sodium amoxycillin in aqueous isopropyl alcohol, as described in Belgian Pat. No. 857,370. In that process the concentration of sodium amoxycillin in the solution to be spray-dried will normally be in the range 5 to 25% w/w and the ratio of isopropanol to sodium amoxycillin present in the solution to be spray-dried will normally be 5:3 to 3:3 w/w.

Alternatively, the sodium amoxycillin may be precipitated from a solution in an inert organic solvent of a conventional tertiary amine salt of amoxycillin using a conventional precipitant such as an alkalimetal alkoxide of salt of a carboxylic acid such as sodium ethylhexanoate.

An alternative way of carrying out the present invention uses the penicillin of formula (I) in the free acid form either as a specific hydrate or otherwise, and a soluble penicillin salt is then formed in situ in the injectable solution of the invention by reconstituting the penicillin with an aqueous solution of benzyl alcohol which also contains about one equivalent of a basic salt.

Accordingly, from a third aspect, the invention provides a two-pack container or two-part syringe wherein one pack or part contains a penicillin of formula (I) herein in a solid free acid form, and the second part contains an aqueous solution of benzyl alcohol and substantially one equivalent of a basic pharmaceutically acceptable salt, such that mixing the contents of the two packs or parts produces an aqueous solution of a salt of the penicillin and from 1 to 10% of benzyl alcohol.

In a preferred embodiment of this third aspect of the invention of penicillin is amoxycillin either as a specific hydrate, e.g. trihydrate or otherwise and the pharmaceutically acceptable salt is a sodium salt. Examples include sodium bicarbonate, sodium carbonate, trisodium phosphate and sodium glycinate.

If necessary small quantities of pharmaceutically acceptable compounds may also be included in the sterile solutions of the first and second aspects of the invention, in order to produce isotonic solutions. Suitable salts include sodium chloride, sodium citrate and glucose.

The injectable solution of the invention should normally contain from 5 to 50%, preferably about 10 to 30%, by weight of penicillin salt, preferably the sodium salt, that is, from about 50 to 500 mg preferably about 100 to 300 mg of penicillin per ml of solvent. Normally, each injectable dose of penicillin should contain from 125 mg to 5 g thereof. Typical unit dosages are 250 mg, 500 mg and 1 g. The aforesaid twin-pack or two-part syringe normally comprises one unit containing such quantity of the penicillin, and the other unit should contain from 0.25 ml to 20 ml of the solution of benzyl alcohol, which if desired contains a salt as hereinbefore indicated.

The invention also provides a process for the preparation of the present pharmaceutical compositions which process comprises mixing a pencillin of formula (I) or salt thereof with an aqueous sterile solution of benzyl alcohol, the proportion of benzyl alcohol being such that the alcohol forms 1 to 10% of the resultant solution.

In a further aspect the invention provides a process for the preparation of the present two-pack container or two-part syringe, which process comprises packing a penicillin of formula (I) or salt thereof as a dry powder into one pack or part, and placing an aqueous solution of benzyl alcohol in the other pack or part, the proportion of benzyl alcohol being such that the alcohol forms 1 to 10% of the contents of the packs or parts when mixed.

In another aspect the invention provides a process for the preparation of a two-pack container or two-part syringe for providing an injectable solution of a salt of amoxycillin according to the present invention, which process comprises packing amoxycillin in solid form into one pack or part, and placing the aqueous solution of benzyl alcohol and substantially one equivalent of a basic pharmaceutically acceptable salt in the other pack or part, the proportion of benzyl alcohol being such that the alcohol forms 1 to 10% of the contents of the packs or parts when mixed.

Because benzyl alcohol is a readily oxidisable compound the injectable solutions of this invention are preferably prepared and stored under an inert gas atmosphere.

The enhanced blood levels achieved by intramuscular injection of the solutions according to this invention can be demonstrated by the following experiment, conducted with amoxycillin compositions.

Eight human subjects each received by intramuscular injection the following:

(a) 1 g of sodium amoxycillin in 5 ml of an aqueous solution containing 3% of benzyl alcohol; and, after an interval of one week, (b) 1 g of sodium amoxycillin in 5 ml of sterile water.

Blood samples were taken after 10, 20, 30, 45 minutes, 1 hour, 1 hour 15 minutes, 1 hour 30 minutes, 2, 3, 5 and 7 hours. Blood levels of amoxycillin were determined (by the method of Grove and Randall) in these samples and are shown in Table 1.

TABLE 1

| | Mean blood levels (± error) of amoxycillin after: | | | | | | | | | | |
|---|---|---|---|---|---|---|---|---|---|---|---|
| | 10 min | 20 min | 30 min | 45 min | 1 h | 1 h 15 | 1 h 30 | 2 h | 3 h | 5 h | 7 h |
| Amoxycillin in sterile water | 12.1 | 8.6 ± 3.2 | 10.9 ± 2.8 | 12.9 ± 2.6 | 14 ± 2.4 | 14.1 ± 1.7 | 12.8 ± 1.2 | 10.9 ± 0.8 | 7.5 ± 0.5 | 3.1 ± 0.3 | 1.3 ± 0.2 |
| Amoxycillin in solution in benzyl alcohol | 9.9 ± 1.6 | 15.9 ± 1.8 | 20.1 ± 1.8 | 21.6 ± 1.5 | 22.3 ± 1.5 | 19.6 ± 1.4 | 17.1 ± 1.2 | 12.9 ± 0.8 | 8 ± 0.4 | 2.6 ± 0.3 | 0.8 ± 0.1 |

It can be seen that the peak blood level (maximum concentration) of amoxycillin produced after injection in benzyl alcohol solution appears earlier and is significantly more elevated than that produced on injection in water alone. These differences are statistically significant at probability less than 0.01 (test of Wilcox).

Thus the use of an injectable solution containing benzyl alcohol results in the peak serum level of being achieved more rapidly and at a statistically higher concentration. In addition the formulations render an intramuscular injection less painful.

The following Examples illustrate this invention.

EXAMPLE 1

An injectable preparation of amoxycillin was prepared as follows:

Formula for one litre of vehicle:

| | |
|---|---|
| benzyl alcohol | 30 g |
| water for injectable preparations, sufficient to make up | 1000 ml |
| nitrogen | qs |

The benzyl alcohol is dissolved in approximately 900 ml of water which has previously been degassed by boiling and cooled in a current of nitrogen. The solution is made up to 1000 ml, filtered under aseptic conditions in nitrogen, and apportioned into ampoules, which are then sealed. The contents of the ampoules are added to other vials containing sodium amoxycillin, so that the subsequent solutions contain 1 g of sodium amoxycillin in 5 ml of 3% benzyl alcohol solution. The solution is immediately employed for intramuscular injections.

EXAMPLE 2

A sterile twin vial presentation is produced by sealing 1 g of sodium amoxycillin in one ampoule and 5 ml of a sterile aqueous solution of 3% benzyl alcohol in a second ampoule. The two sealed ampoules are attached to a card or pack containing instructions for use.

Biological Properties of Benzyl Alcohol Solutions

(a) TOXICOLOGY

1 Acute toxicity

No mortality is observed in mice or rats treated at the rate of 750 mg/kg of benzyl alcohol in 3% solution (viz 25 ml/kg of solution) by the intramuscular route.

1 Sub-acute toxicity

Over a period of 2 weeks, 10 male rats and female rats receive 150 mg/kg of benzyl alcohol, that is to say 5 ml/kg of 3% aqueous solution by the intramuscular route. No abnormal symptom appears. All the variations observed from the weight point of view, from the haematological point of view and from the point of view of blood and urine biochemistry are within the limits of physiological variations. Within the context of the anatomopathological examination, the liver, kidneys, spleen, lungs, suprarenals, testicles and ovaries are normal.

(b) PHARMACOLOGY

The local anaesthetic activity was investigated:

1 by infiltration, in the guinea pig, of 0.1 ml of 3% benzyl alcohol solution: local anaesthesia is obtained and maintained in the presence of amoxycillin.

2 on the cornea of the eye of the rabbit: no surface anaesthesia.

The benzyl alcohol solution thus shows infiltration anaesthesia and not surface anaesthesia.

I claim:

1. An antibiotic pharmaceutical composition adapted for intramuscular injection which comprises an aqueous sterile solution in the proportions of 3% benzyl alcohol, and 1 gram of amoxycillin or a salt thereof, said composition upon injection providing an enhanced blood level and a more rapid peak level of amoxycillin than the same solution without benzyl alcohol.

2. A composition according to claim 1, characterised in that the amoxycillin salt is the trisodium phosphate salt.

3. A two pack container or two-part syringe wherein one pack or part contains amoxycillin or a salt thereof in the form of a dry powder and the second pack or part contains an aqueous solution of benzyl alcohol, the relative proportions being such that mixing the contents of the two packs or parts produces an injectable aqueous solution in the proportion of 1 gram of amoxycillin or salt thereof to 3% of benzyl alcohol.

* * * * *